(12) United States Patent
Kelly et al.

(10) Patent No.: US 6,910,884 B2
(45) Date of Patent: Jun. 28, 2005

(54) LOW PROFILE ORTHODONTIC APPLIANCE

(75) Inventors: John S. Kelly, Arcadia, CA (US); Oliver L. Puttler, La Crescenta, CA (US); John A. Verdouw, Ontario, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 202 days.

(21) Appl. No.: 10/324,265

(22) Filed: Dec. 19, 2002

(65) Prior Publication Data

US 2004/0121278 A1 Jun. 24, 2004

(51) Int. Cl.⁷ .................................................. A61L 3/00
(52) U.S. Cl. ................................. 433/9; 433/8; 433/17
(58) Field of Search ............................. 433/8, 9, 16, 17

(56) References Cited

U.S. PATENT DOCUMENTS

| | | |
|---|---|---|
| 3,765,091 A | 10/1973 | Northcutt |
| 3,964,165 A | 6/1976 | Stahl |
| 4,219,617 A | 8/1980 | Wallshein |
| 4,302,532 A | 11/1981 | Wallshein |
| 4,531,911 A | 7/1985 | Creekmore |
| D290,040 S | 5/1987 | Kelly |
| 4,820,151 A | 4/1989 | Pospisil |
| 4,936,773 A | 6/1990 | Kawaguchi |
| D315,957 S | 4/1991 | Kelly et al. |
| 5,059,119 A | 10/1991 | Snead |
| 5,094,614 A | 3/1992 | Wildman |
| 5,151,028 A | 9/1992 | Snead |
| 5,161,969 A | 11/1992 | Pospisil et al. |
| D331,975 S | 12/1992 | Pospisil |
| 5,320,525 A | 6/1994 | Förster |
| 5,380,196 A | 1/1995 | Kelly et al. |
| 5,439,379 A | 8/1995 | Hansen |
| 5,456,599 A | 10/1995 | Hanson |
| 5,522,725 A | 6/1996 | Jordan et al. |
| 5,556,277 A | 9/1996 | Yawata et al. |
| 5,618,175 A | 4/1997 | Reher et al. |
| 5,707,231 A | 1/1998 | Watt et al. |
| 5,746,594 A | 5/1998 | Jordan et al. |
| 5,820,371 A | 10/1998 | Förster |
| 5,910,007 A | 6/1999 | Shimodaira et al. |
| 5,911,574 A | 6/1999 | Casey |
| 6,053,729 A * | 4/2000 | Brehm et al. .................. 433/9 |
| 6,206,690 B1 | 3/2001 | Vargas |
| 6,217,322 B1 | 4/2001 | Kesling |
| 6,241,516 B1 | 6/2001 | Orikasa et al. |
| 6,280,185 B1 | 8/2001 | Palmer et al. |
| 6,709,268 B2 | 3/2004 | Pospisil et al. |
| 2002/0150858 A1 * | 10/2002 | Jordan et al. .................. 433/9 |

FOREIGN PATENT DOCUMENTS

| | | |
|---|---|---|
| DE | 19856794 | 6/2000 |
| EP | 0624354 | 11/1994 |
| EP | 0976368 | 2/2000 |
| WO | WO 01/22901 | 5/2001 |

OTHER PUBLICATIONS

3M Unitek Product Catalog 2001–2002, pp. 3–1 to 3–17.
GAC Orthodontic Products, (1983), pp. A1, E1–E10.
GAC Orthodontic Catalog Copyright 1997, pp. 58–77.
U.S. Appl. No. 10/324,655, filed Dec. 19, 2002.

* cited by examiner

Primary Examiner—Cary E. O'Connor
Assistant Examiner—Candice C Stokes
(74) Attorney, Agent, or Firm—James D. Christoff

(57) ABSTRACT

An orthodontic appliance such as a bracket or buccal tube has an overall, low profile shape. The appliance includes a base having a thickness that is less in regions adjacent the archwire slot as compared to remaining regions. In certain embodiments, the base is provided with protrusions that extend into the archwire slot for controlling rotation of the associated tooth. The resulting low profile of the appliance enhances its aesthetic appearance and helps to avoid impingement of the appliance and the attached archwire on adjacent soft tissue in the oral cavity.

62 Claims, 5 Drawing Sheets

LOW PROFILE ORTHODONTIC APPLIANCE

BACKGROUND OF THE INVENTION

1. Field of the Invention

This invention broadly relates to an appliance that is secured to a tooth during the course of orthodontic treatment. More particularly, the present invention is directed to an orthodontic appliance having a compact, low profile such that the appliance lies close to the tooth surface.

2. Description of the Related Art

Orthodontia is a specialized field within the general subject area of dentistry. Orthodontic treatment involves movement of malpositioned teeth to correct locations along the dental arch. Orthodontic treatment can result in improved occlusion for the patient as well as a more pleasing aesthetic appearance.

One type of orthodontic treatment involves the use of a set of components that are collectively known as "braces". In this type of treatment, small slotted devices known as brackets are secured to the patient's anterior, cuspid and bicuspid teeth. An archwire is received in the slots of the brackets and forms a track to guide movement of the teeth to desired positions.

Each end of an orthodontic archwire is often received in an enclosed elongated passageway of a small device known as buccal tube. Buccal tubes are connected to the patient's molar teeth. The enclosed passageway helps prevent the end of the archwire from contacting the patient's soft tissue in the oral cavity, which might otherwise lead to pain and injury. In some instances, buccal tubes are provided with a convertible cap along one side of the passageway that can be opened in order to convert the tube into a bracket when desired.

Orthodontic appliances such as brackets and buccal tubes typically include a base, a body extending outwardly from the base and support structure for connecting the appliance to the archwire. One type of base, known as a "direct bond" base, is adapted to secure the appliance directly to the enamel surface of a tooth by an adhesive. Another type of base, known as a "welding base", is adapted to be welded to a metallic orthodontic band that encircles the patient's tooth.

A variety of archwire support structures are also known. In the case of buccal tubes, the archwire support structure may be a cylindrical member having internal wall sections that define an enclosed archwire slot or passageway. Other types of buccal tubes have archwire support structure that comprises an elongated rectangular block with wall sections defining an archwire slot or passageway. Buccal tubes with convertible caps often have small wings known as tiewings that can be used to ligate the archwire to the buccal tube once the cap has been removed.

In the case of orthodontic brackets, the archwire support structure often includes wall sections that define three sides of the archwire slot while the fourth side is open for insertion of the archwire. In some instances, the wall sections are located between one or more pairs of tiewings. In other instances, the wall sections are located in the center of the bracket and offset from the tiewings. An example of the former construction is shown in U.S. Pat. No. 5,746,594, and an example of the latter construction is illustrated in U.S. Design Pat. No. 290,040.

Over the years, many attempts have been made to improve the aesthetic appearance of braces. To this end, manufacturers have reduced the size of the brackets so that they are more difficult to see when in place in the oral cavity. This reduction in size can also help increase patient comfort because it is less likely that the bracket will unduly impinge upon adjacent soft tissue.

A variety of low profile orthodontic appliances have been proposed in the past. In some appliances, manufacturers have reduced the overall depth of the bracket in a buccolabial direction (i.e., in a direction toward the patient's lips or cheeks) by reducing the size of the body located between the base of the appliance and the archwire support structure. Such construction results in the archwire support structure being located relatively close to the base.

In other instances, the manufacturers have eliminated the body that is conventionally located between the archwire support structure and the base. For example, one commercially available buccal tube appliance comprises an elongated, generally "U"-shaped structure resembling an inverted three-sided trough that is directly welded to a base. In this appliance, the buccolabial side of the base serves as the fourth wall for the archwire slot such that the archwire is surrounded on all four sides.

However, many of the low profile appliances known in the past are not considered satisfactory. For example, the appliance mentioned in the preceding paragraph is not entirely satisfactory because the buccolabial side of the base, including the portion of the base within the archwire slot, has a convex, curved configuration that matches the shape of the tooth. An archwire received in the archwire slot of this appliance may bear against the convex-shaped base along only a fraction of the length of the archwire slot. As a consequence, precise control over movement between the archwire and the appliance is difficult to attain and the teeth may not shift to desired positions.

As can be appreciated, there is a need in the art for an orthodontic appliance that has a relatively low profile, and yet provides reliable, precise control over movement of the associated teeth.

SUMMARY OF THE INVENTION

The present invention overcomes the above noted disadvantages of conventional orthodontic appliances by provision of an appliance having a novel base. In one aspect of the invention, the base has a thickness that varies in different regions of the base so that the archwire can be received in a position closer to the tooth surface than might be otherwise possible. The variance in thickness in the base may be carried out by modifying the tooth-facing side of the base, or by modifying the opposite side of the base, or by modifying both sides.

In another aspect of the invention, the base of the appliance is provided with one or more protrusions that extend outwardly in a buccolabial direction. Examples of suitable protrusions include elongated ridges, rounded bumps, posts, ramps and platforms. The protrusions serve as a bearing surface for the adjacent side of the archwire so that firm, precise control over movement of the associated teeth can be attained. At the same time, the low profile characteristics of the appliance are maintained.

In more detail, the present invention is directed in one embodiment to an orthodontic appliance that comprises a base having a first tooth-facing side and a second side opposite that first side. The base also has a number of cavities that extend from the first side in a direction toward the second side, and the cavities have a certain depth in a buccolabial-lingual direction. An archwire support is connected to the base. The support has an occlusal wall section (i.e., a wall section located next to the outer tip of the tooth) and a gingival wall section (i.e., a wall section located next to the patient's gums or gingiva). An archwire slot extends between the occlusal wall section and the gingival wall section in a generally mesial-distal direction (i.e., in directions toward and away from the middle of the dental arch, following along the path of the arch). The archwire slot has a tooth-facing side. The base has a certain thickness in directions along a buccolabial-lingual reference axis between the first side and the second side. The thickness of the base in at least one region next to the tooth-facing side of the archwire slot is less than the thickness of the base in at least one remaining region of the base. The depth of at least some of the cavities varies in corresponding relationship to the variance of the thickness of the base.

In another embodiment of the invention, an orthodontic appliance comprises a base having a tooth-facing surface. The base also has a number of cavities with a certain depth in a buccolabial-lingual direction. An archwire support is connected to the base and has an occlusal wall section and a gingival wall section. An archwire slot extends between the occlusal wall section and the gingival wall section in a generally mesial-distal direction and has a tooth-facing side. The base has a certain thickness in directions along a buccolabial-lingual reference axis. The thickness of the base varies in regions located next to the tooth-facing side of the archwire slot. The depth of at least some of the cavities varies in corresponding relationship to the variance of the thickness of the base.

An orthodontic appliance according to another embodiment of the invention comprises a base having a first, tooth-facing side and a second side opposite the first side. The base also has a number of cavities extending from the first side in a direction toward the second side, and the cavities have a certain depth in a buccolabial-lingual direction. An archwire support is connected to the second side of the base. An archwire slot extends across the appliance in a generally mesial-distal direction. The archwire slot has a side next to the tooth that extends along a path located at least partially between the first side and the second side of the base. At least some of the cavities located in regions lingually of the archwire slot have a depth that is less than the depth of the cavities located in regions offset from the archwire slot.

The present invention in another embodiment is also directed to an orthodontic appliance. In this embodiment, the appliance comprises a base having a tooth-facing surface and an archwire support connected to the base for receiving an archwire. An archwire slot extends across the archwire support in a generally mesial-distal direction. The base includes a plurality of cavities having a certain depth in directions along a buccolabial-lingual reference axis. The depth of at least some of the cavities located in regions lingually of the archwire slot is less than the depth of at least some of the remaining cavities located in regions lingually of the archwire slot.

An additional embodiment of the invention is also directed toward an orthodontic appliance that comprises a base having a first, tooth-facing side and a second side opposite the first side. An archwire support is connected to the base and has an occlusal wall section and a gingival wall section. An archwire slot extends between the occlusal wall section and the gingival wall section in a generally mesial-distal direction and has a lingual side. The first side of the base includes at least one protrusion that extends in a direction toward the archwire slot.

Another embodiment of the invention is also directed toward an orthodontic appliance. In this embodiment, the appliance includes a first, tooth-facing side and a second side opposite the first side. At least two tiewings are directly connected to the base. Each of the tiewings has an overall, generally "L"-shaped configuration. An archwire slot extends between at least two of the tiewings in a generally mesial-distal direction and has a tooth-facing side defined by the base.

These and other aspects of the invention will be described in more detail in the paragraphs that follow and are illustrated in the accompanying drawings.

DETAILED DESCRIPTION OF THE PREFERRED EMBODIMENTS

Figure 1:
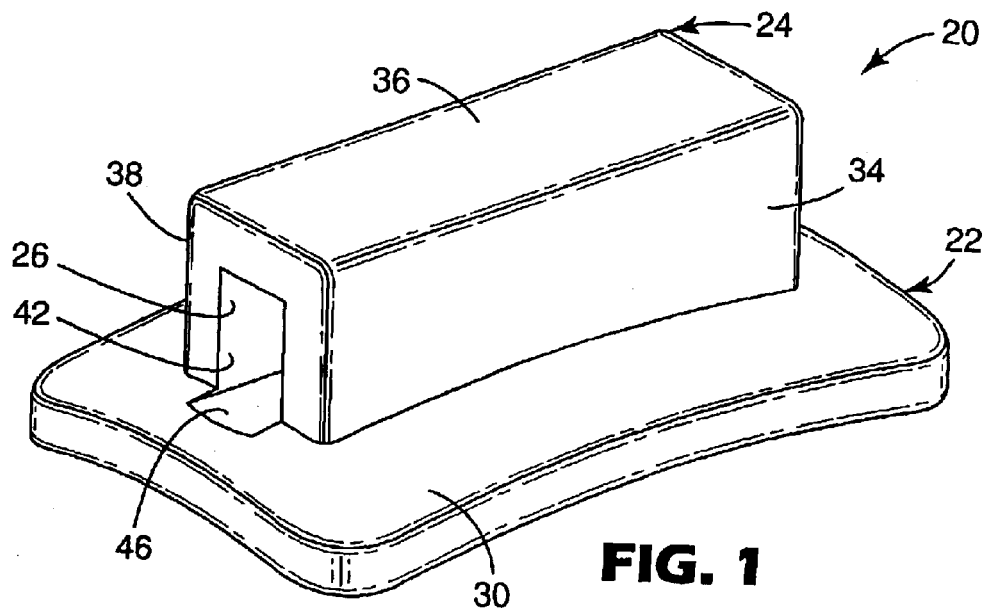
FIG. 1 is a perspective view of a low profile orthodontic appliance that is constructed in accordance with one embodiment of the present invention, looking at the appliance in a direction toward its buccolabial, mesial and occlusal sides.
Figure 2:
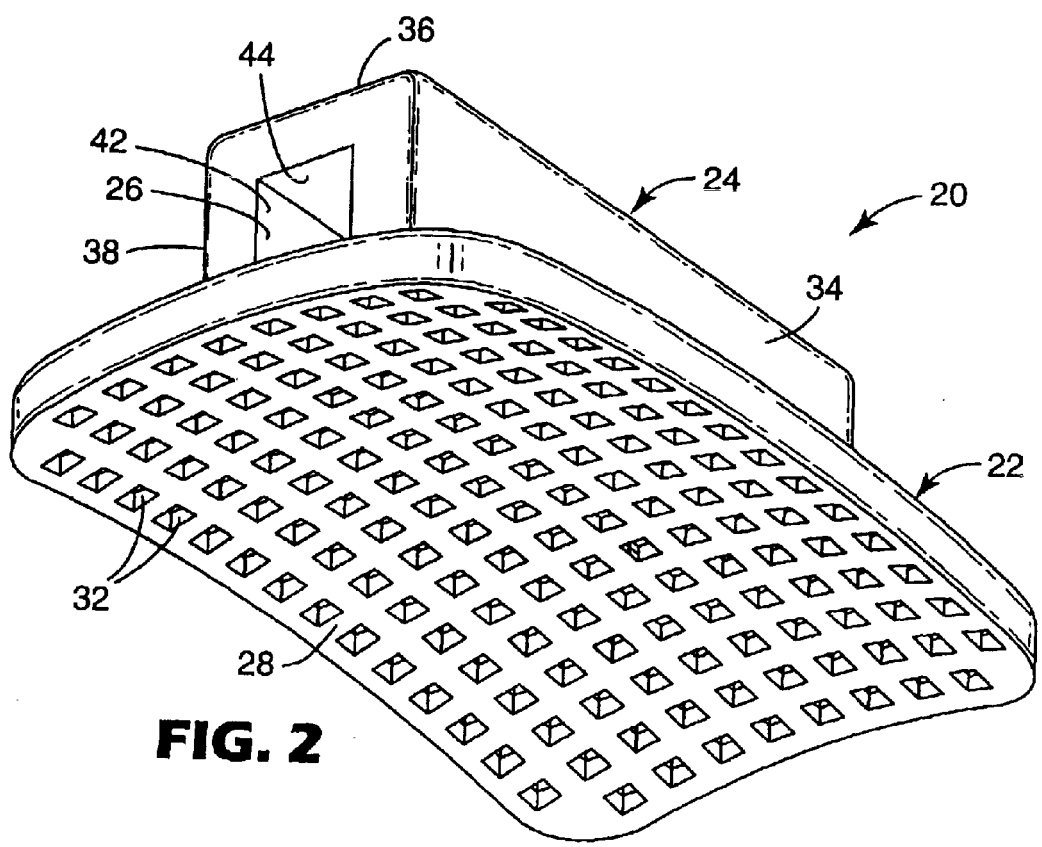
FIG. 2 is a perspective view of the orthodontic appliance shown in FIG. 1, looking at the appliance toward its lingual, mesial and occlusal sides.
Figure 3:
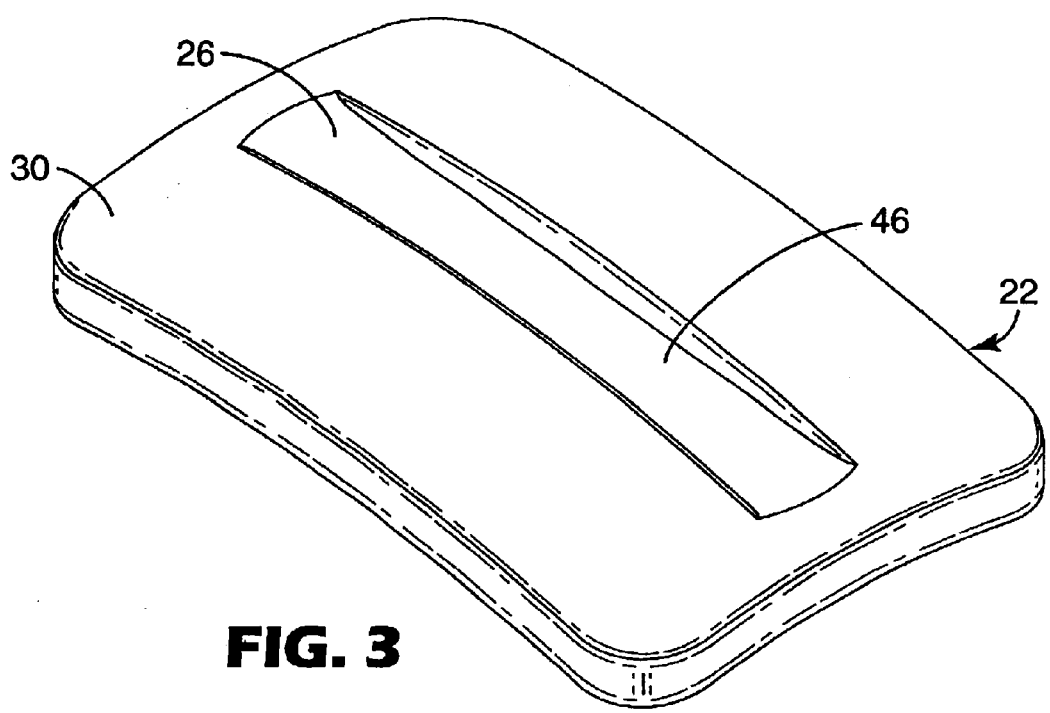
FIG. 3 is a perspective view of a base alone of the appliance depicted in FIGS. 1 and 2, looking at the base in a direction toward its buccolabial, mesial and gingival sides.

An orthodontic appliance according to one embodiment of the present invention is illustrated in FIGS. 1 and 2 and is broadly designated by the numeral 20. The appliance 20 includes a base 22 and an archwire support 24 that is connected to the base 22. An elongated archwire slot 26 extends through the archwire support 24 for receiving an archwire.

In more detail, the base 22 includes a first, tooth-facing side 28 that is illustrated in FIG. 2 and a second side 30 that is opposite to the first side 28. The second side 30 is shown in FIG. 1. In the illustrated example, the appliance 20 is adopted to be secured to a buccolabial side of a tooth. Consequently, the first side 28 of the base 22 in this example can also be deemed a lingual side (i.e., a side facing the patient's tongue) and the second side 30 can be deemed a buccolabial side (i.e., a side facing the patient's lips or cheeks).

As shown in FIG. 2, the first side 28 of the base 22 is provided with a series of cavities 32 for receiving a portion of an orthodontic adhesive that is used to affix the appliance 20 to the enamel of a patient's tooth. The cavities 32 are arranged in a rectangular array and have a square configuration when viewed in a buccolabial direction. However, other arrays and shapes are also possible. For example, the cavities could be arranged in a diagonal array and/or have a circular, oval or rectangular shape when viewed in a buccolabial direction.

Alternatively, the cavities 32 may comprise two or more series of elongated grooves instead of the discrete small cavities 32 shown in FIG. 2. The grooves may be arranged in a parallel array or may be arranged in a cross-over array where some of the grooves intersect with other grooves. Examples of elongated grooves arranged in a cross-over array are described in U.S. Design Pat. No. 331,975 which is expressly incorporated by reference herein. As a further option, the cavities 32 may be interconnected by pores that extend through the interior of the base 22 or by open channels that lie along the exterior surface of the first side 28 of the base 22. Additionally, the cavities 32 may be established by spaces between protrusions that extend outwardly from the first side 28 in a direction away from the second side 30.

In addition, the base 22 including the cavities 32 may include additional structure or aspects that further enhance the bond of the appliance 20 to the patient's tooth surface. For example, the base 22 including the surfaces within the cavity 32 may be etched with a chemical etchant or with laser etching apparatus, or roughened with sandblasting apparatus. As an additional example, the base 22 including the cavities 32 may be coated with a primer or other composition that serves to enhance the bond between the orthodontic adhesive and the appliance 20.

Figure 4:
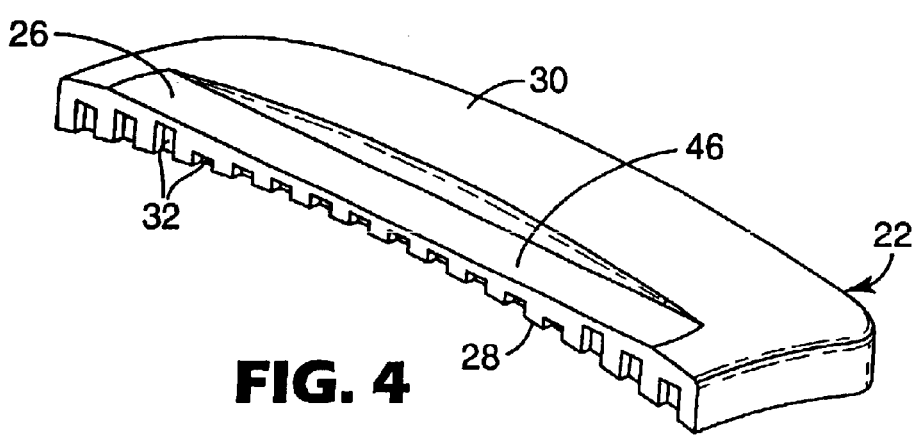
FIG. 4 is a perspective cross-sectional view of the base illustrated in FIG. 3, looking at the base in the same direction as the illustration of FIG. 3.
Figure 5:
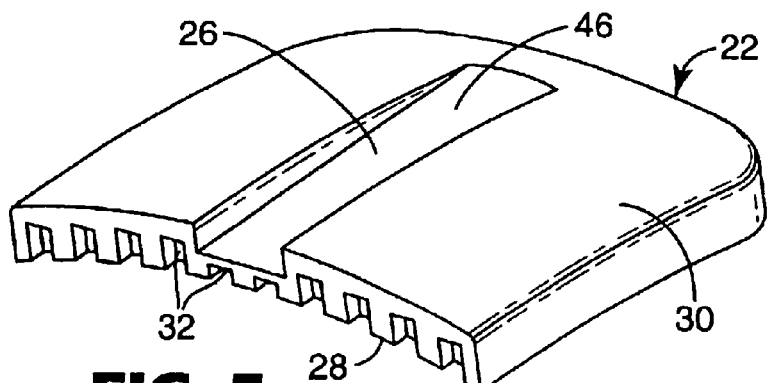
FIG. 5 is another perspective cross-sectional view of the base shown in FIG. 3, wherein the view is taken along a reference plane that is perpendicular to the plane of view of FIG. 4.

Preferably, the first side 28 of the base 22 has a shape that matches the configuration of the tooth surface for which the appliance 20 is intended. In the example shown in the drawings, the first side 28 has a concave, compound contour that is curved in directions adapted to mate with the convex shape of a molar tooth. One of the curves can be viewed in a reference plane parallel to the occlusal plane of the patient when the appliance 20 is mounted on a tooth, and this curve is depicted in perspective view in FIG. 4. The remaining curve can be viewed in a reference plane perpendicular to the occlusal plane and is depicted in perspective view in FIG. 5. However, in certain instances (such as in appliances intended for anterior teeth), the base may be curved along only one direction or alternatively have a flat configuration.

The archwire support 24 in this embodiment is a rectangular "U"-shaped member having three sides: an occlusal side 34, a buccolabial side 36 and a gingival side 38. The archwire support 24 extends in a longitudinal direction across the base 22. A lingual edge of the occlusal side 34 and a lingual edge of the gingival side 38 are integrally connected directly to the second side 30 of the base 22. As shown, the archwire support 24 does not include a lingual side that might otherwise be located adjacent the second side 30 of the base 22. Optionally, the archwire support 24 is located laterally offset in an occlusal or gingival direction from the middle of the base 22.

The occlusal side 34 of the archwire support 24 includes an occlusal wall section (not shown) and the gingival side 38 includes a gingival wall section 42 that is illustrated in FIG. 1. The buccolabial side 36 of the archwire support 24 includes a buccolabial wall section 44 (FIG. 2). Preferably, but not necessarily, the wall sections are flat and have widths that match the shape of a selected rectangular archwire to be received in the archwire slot 26. Additionally, the occlusal wall section and the gingival wall section 42 preferably are parallel to each other.

The archwire slot 26 is defined by the occlusal wall section, the gingival wall section 42, the buccolabial wall section 44 as well as a tooth-facing or lingual wall section 46 that is shown in FIGS. 1 and 3–5. The lingual wall section 46 is not part of the archwire support 24, but instead is part of the base 22. Preferably, the lingual wall section 46 is flat and extends in a reference plane that is parallel to the labial wall section 44.

Alternatively, the lingual wall section 46 as well as one or more of the remaining wall sections may include one or more ridges or grooves (not shown) for engaging the archwire. Examples of such grooves are shown in FIGS. 8–11 of U.S. Design Pat. No. 315,957 which is incorporated by reference herein. Preferably, however, the wall sections contact the archwire in sufficient areas along the length of the archwire slot 26 so that good control between movement of the appliance 20 and movement of the archwire is afforded.

As shown in FIGS. 1, 3, 4 and 5, the lingual wall section 46 extends below the second side 30 of the base 22 in a lingual direction. Consequently, the thickness of the base 22 in regions located lingually of the lingual wall section 46 is less than the thickness of the base 22 in remaining regions of the base 22. The thickness of the base 22 for this purpose is determined in directions parallel to a buccolabial-lingual reference axis. Optionally, the thickness of the base 22 is essentially uniform (ignoring the cavities 32) except for regions of the base 22 that are located lingually of the lingual wall section 46.

In the illustrated embodiment, the second side 30 of the base 22 is convex and the thickness of the base 22 is smallest in regions next to the center of the lingual wall section 46 (for this purpose, the center of the wall section 46 is determined in directions along a mesial-distal reference axis). However, other constructions are also possible. For example, if the appliance 20 is intended to be placed on the tooth at a location that is offset the mesial-distal center of the tooth or if the appliance 20 is intended to provide what is known as offset rotation, the thickness of the base 22 may be smallest in regions that are located on the lingual side of the lingual wall section 46, but adjacent the mesial or distal end of the same. In these examples, the thickness of the base 22 varies in regions located lingually of the lingual wall section 46 in accordance with the location of that region in directions along the longitudinal axis of the archwire slot 26.

Additionally, the depth (i.e. the overall depth) of the cavities 32 in directions along a buccolabial-lingual reference axis varies in corresponding relationship to the thickness of the base 22. In particular, the depth of the cavities 32 is the least in regions where the thickness of the base 22 is the smallest. In the embodiment illustrated in the drawings, and particularly with reference to FIG. 4, It can be observed that the depth of the cavities 32 that are located near the mesial-distal center of the archwire slot 26 is less than the depth of the remaining cavities 32, including the cavities adjacent the mesial and distal ends of the lingual wall section 46. The depth of at least some of the cavities 32 located in regions lingually of the archwire slot 26 is less than the depth of the cavities 32 that are located in regions offset from the archwire slot 26 in an occlusal or gingival direction. Optionally, the depth of the cavities 32 progressively increases as the thickness of the base 22 increases. As another option, the depth of the cavities 32 may progressively increase as the occlusal edge and/or gingival edge of the appliance 20 is approached.

The features of the appliance 20 described above provide a significant advantage in that the overall height of the appliance 20 in a buccolabial direction is smaller than might be otherwise possible. In particular, the lingual wall section 46, being located below the second side 30 of the base 22 in a lingual direction, enables the archwire slot 26 to be relatively close to the first side 28 of the base 22. The varying thickness of the base 22 as well as the varying depth of the cavities 32 also enables such advantages to be realized.

Importantly, control over movement of the appliance 20, the archwire and the associated tooth need not be compromised by following the principles of the present invention. In particular, since the lingual wall section 46 is parallel with the buccolabial wall section 44, the archwire maintains good bearing contact with the appliance 20. As such, forces exerted by the archwire on the appliance 20 are transferred without undue tolerance or "slop" so that precise control over movement of the archwire or the associated teeth can be attained.

Figure 6:
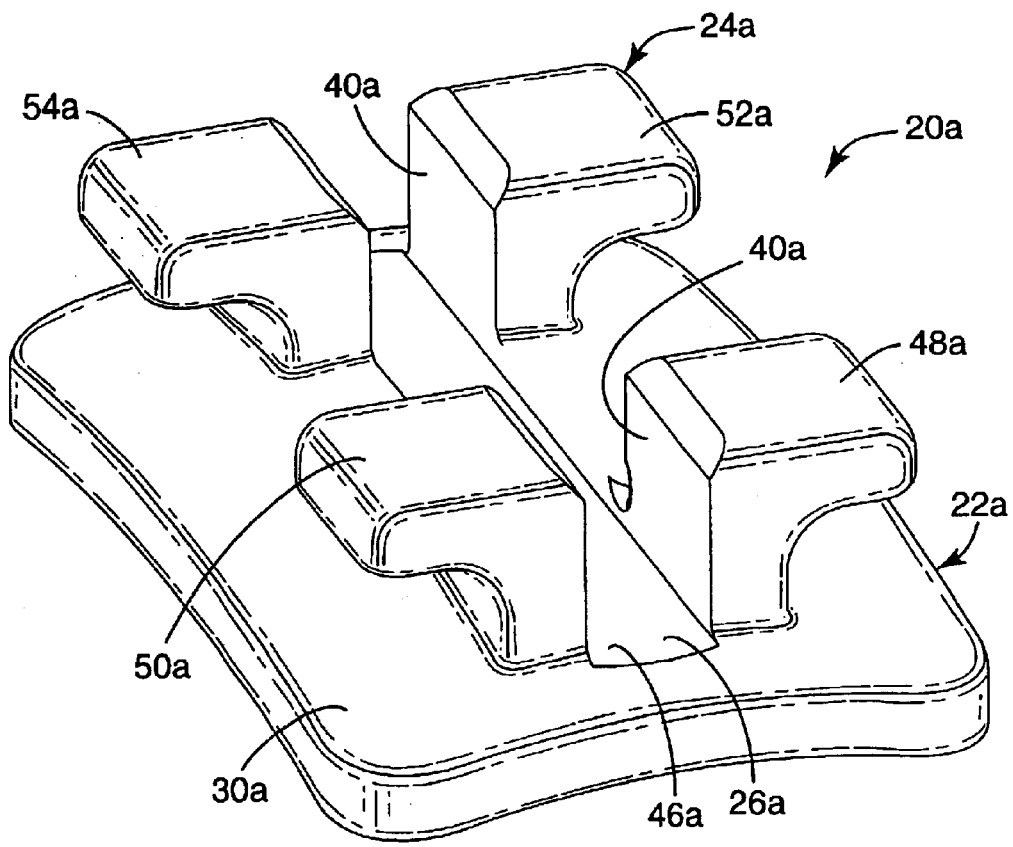
FIG. 6 is a perspective view of a low profile orthodontic appliance according to another embodiment of the invention, looking at the appliance in a direction toward its buccolabial, mesial and gingival sides.
Figure 7:
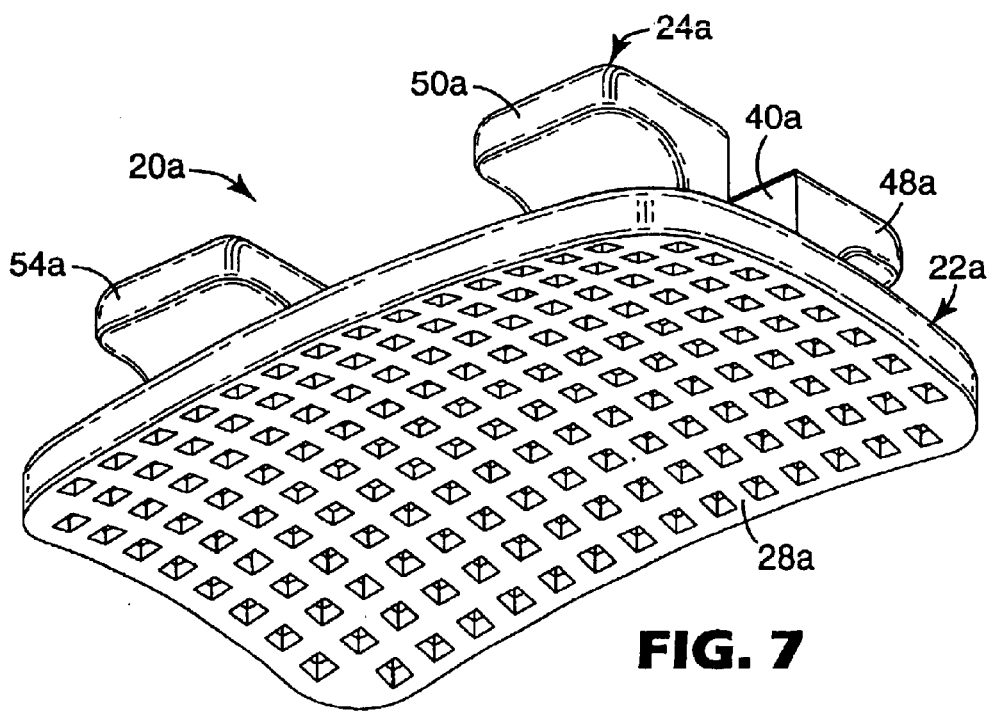
FIG. 7 is another perspective view of the appliance shown in FIG. 6, looking at the appliance in a direction toward its lingual, mesial and gingival sides.
Figure 8:
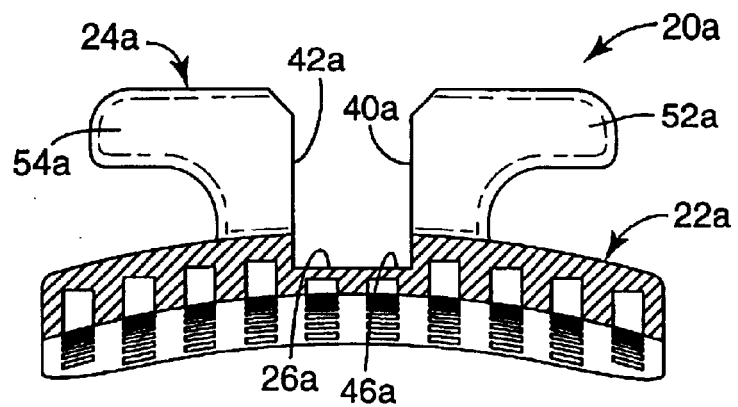
FIG. 8 is a side cross-sectional view of the orthodontic appliance shown in FIGS. 6–7, looking at the appliance in a direction toward its distal side.

A low profile orthodontic appliance 20a according to another embodiment of the invention is illustrated in FIGS. 6, 7 and 8. The appliance 20a includes a base 22a that is essentially the same as the base 20 described above.

However, the appliance 20a has an archwire support 24a that is somewhat different than the archwire support 24 mentioned above. In particular, the archwire support 24a includes a mesial-occlusal tiewing 48a, a mesial-gingival tiewing 50a, a distal-occlusal tiewing 52a and a distal-gingival tiewing 54a. Each of the tiewings 48a–54a has a generally inverted "L"-shaped configuration and a lingual end section that is directly connected to a second or buccolabial side 30a of the base 22a.

An archwire slot 26a extends in a generally mesial-distal direction across the appliance 20a. The archwire slot 26a passes through the space between the tiewings 48a, 50a as well as through the space between the tiewings 52a, 54a. The archwire slot 26a is defined by two occlusal wall sections 40a that are located on the tiewings 48a, 52a respectively, and two gingival wall sections (not shown) that are located on the tiewings 50a, 54a respectively. The archwire slot 26a is also defined by a lingual wall section 46a that is part of the base 22a.

The appliance 20a is a bracket and, as with many brackets, the archwire slot 26a is open along its buccolabial side. In order to couple the archwire to the appliance 20a, a ligature (not shown) is placed across the buccolabial side of the archwire once the archwire is seated in the archwire slot 26a. The ligature is also placed around two or more of the tiewings 48a–54a in order to hold the ligature in place and secure the archwire to the appliance 20a. Conventional, commonly-known ligatures useful for ligating include small elastomeric O-rings and also sections of metallic wire that are formed into a loop by the practitioner.

Advantageously, the tiewings 48a–54a lack undercut areas or notches that are conventionally located on the lingual side of the portions of the tiewings that overhang the base. In other words, the overhanging portions do not have a recess that is located a distance further away from the buccolabial side 30a of the base 22a in a buccolabial direction than the distance between the outer, occlusal or gingival ends of the same tiewings from the buccolabial side 30a of the base 22a. Instead, the lingual sides of the overhanging portions of the tiewings 48a–54a are generally smooth and flat and extend along occlusal-gingival reference axes. Such construction is satisfactory in part due to the recessed lingual wall section 46a, which enables the archwire to be located closer to the first side 28a of the base 22a than might be otherwise possible.

Advantageously, the appliance 20a lacks a body that is conventionally provided between the tiewings and the base. Instead, the tiewings 48a–54a are directly connected to the buccolabial side of the base 22a. Preferably, the appliance 20a is integrally made as a unitary component by a metal injection molding process or a machining process. As an alternative, however, the tiewings 48a–54a maybe manufactured separately and then connected by a welding or brazing operation directly to the base 22a.

Other aspects of the appliance 20a are similar to the appliance 20 mentioned above, including the variance in thickness of the base 22a and the variance in the depth of cavities in the base 22a. Accordingly, the advantages realized in connection with the appliance 20 are afforded to the appliance 20a as well.

Figure 9:
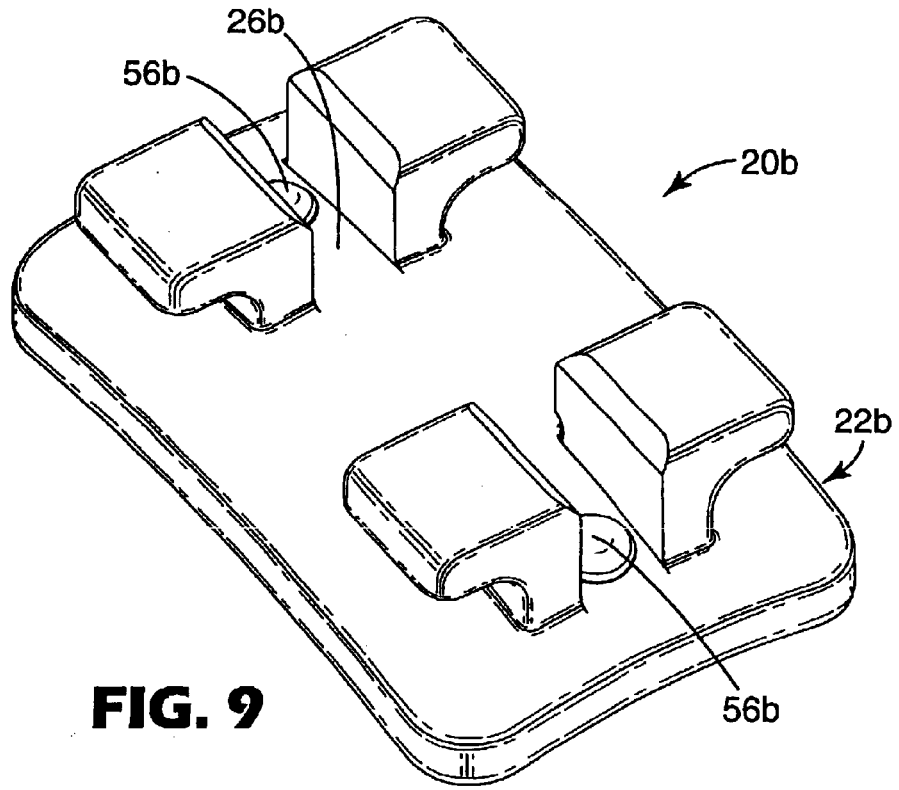
FIG. 9 is a perspective view of a low profile orthodontic appliance according to yet another embodiment of the invention, looking at the appliance in a direction toward its buccolabial, mesial and gingival sides.
Figure 10:
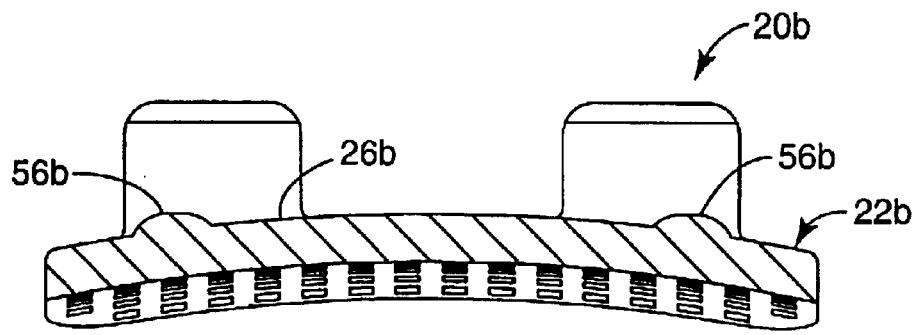
FIG. 10 is a cross-sectional view of the orthodontic appliance depicted in FIG. 9 and taken along a reference plane that bisects an archwire slot of the appliance.

A low profile orthodontic appliance 20b according to another embodiment of the invention is illustrated in FIGS. 9 and 10. Except as described below, the appliance 20b is essentially the same as the appliance 20a.

The appliance 20b has a base 22b with one or more protrusions 56b that extend in a direction toward an archwire slot 26b. In the illustrated embodiment, the base 22b includes two protrusions 56b in the general shape of rounded, semi-spherical bumps. One of the protrusions 56b is located adjacent a mesial end of the archwire slot 26b, and the remaining protrusion 56b is located adjacent the distal end of the archwire slot 26b. However, it is also possible to provide one or more protrusions that are located adjacent only one end of the archwire slot 26b, especially in instances where the appliance is intended to rotate the associated tooth about its long axis during the course of treatment.

Optionally, the protrusions 56b are formed during a metal injection molding process that is carried out when manufacturing the appliance 20b. As another option, the protrusions 56b maybe formed by use of a punch process, wherein a punch tool is placed in contact with a tooth-facing side of the base 22 and urged in a buccolabial direction.

Although not shown in the drawings, the appliance 20b may include an archwire slot that is defined in part by a lingual wall section which extends below the buccolabial side of the appliance base 22 in a lingual direction. For example, the lingual wall section may be similar to the lingual wall sections 46, 46a described above. In those instances, the protrusions 56b may extend in a buccolabial direction from the recessed lingual wall section. As an additional option, the protrusions 56b may be located on the mesial and/or distal side of the lingual wall section.

Figure 11:
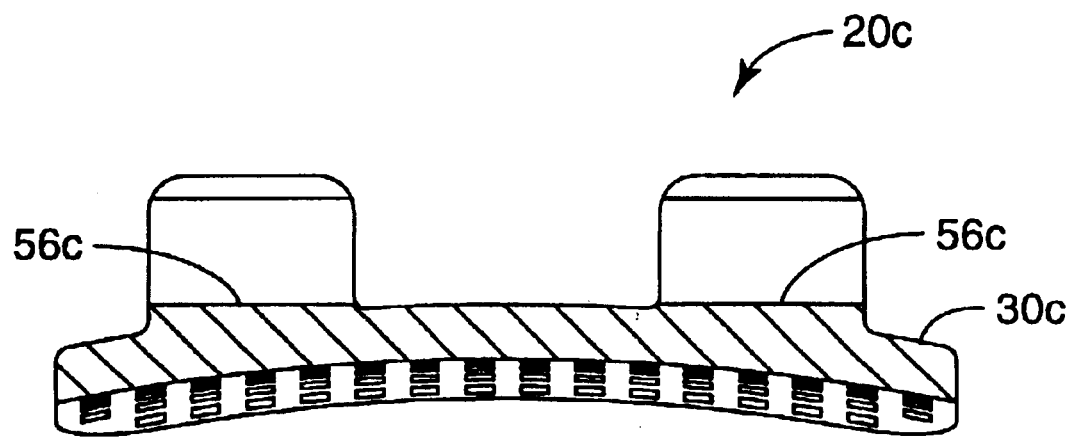
FIG. 11 is a view somewhat similar to FIG. 10 except showing an orthodontic appliance in accordance with still another embodiment of the invention.
Figure 12:
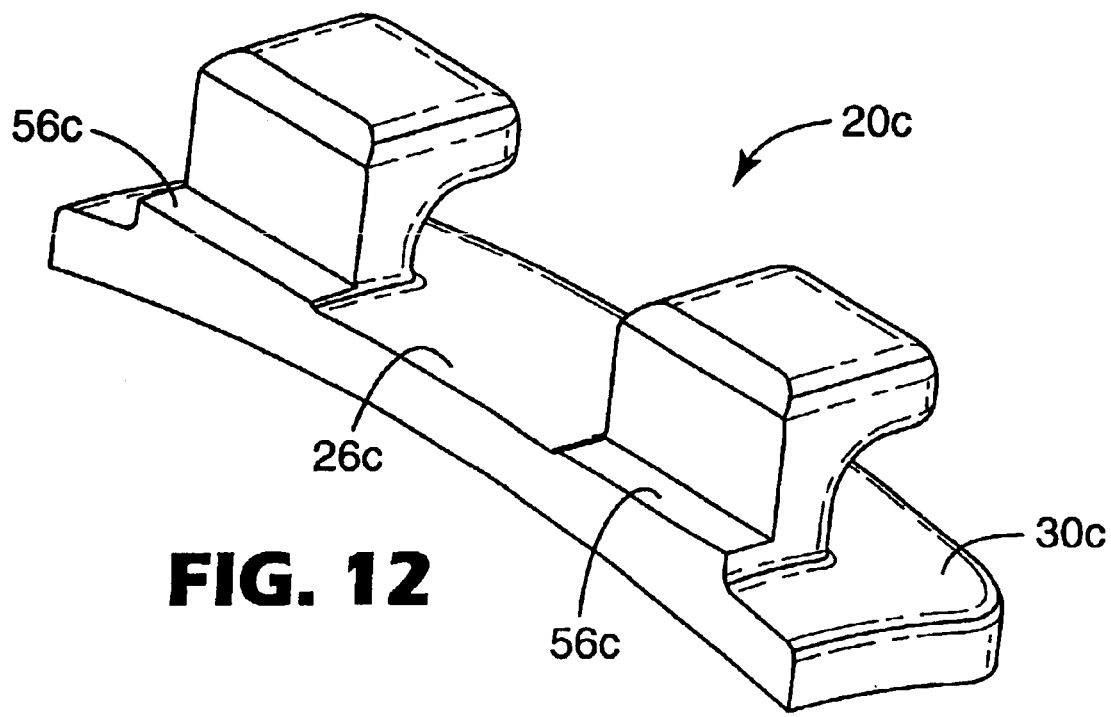
FIG. 12 is a perspective cross-sectional view of the appliance illustrated in FIG. 11.

A low profile orthodontic appliance 20c according to another embodiment of the invention is partially shown in FIGS. 11 and 12. FIG. 11 is a cross-sectional view of the appliance 20c taken in the same direction as the illustration of FIG. 10. Except as set out below, the appliance 20c is the same as the appliance 20b.

The appliance 20c has two protrusions 56c that extend in a buccolabial direction from a base 22c of the appliance 20c. In this embodiment, however, the protrusions 56c are in the form of a ramp of varying thickness in a buccolabial direction. In particular, the thickness decreases as the mesial-distal center of the archwire slot 26c is approached.

The buccolabial surface of each protrusion 56c in this example lies in a flat plane. Although the protrusions 56c vary in thickness, the protrusions 56c are located atop a convex buccolabial side 30c of the base 22c. The variance in thickness of the protrusions 56c is selected in accordance with the curvature of the buccolabial side 30c of the base 22c so that the outermost, buccolabial surfaces of the protrusions 56c lie in a common, flat plane. As a result, the protrusions 56c flatly contact the lingual side of the archwire and enable the archwire to exert firm, precise control over movement of the associated tooth.

As an alternative, the protrusions 56c may be of uniform thickness in a buccolabial direction. Such construction may be desirable, for example, when the buccolabial side 30c is essentially flat instead of convex as shown in the drawings. As an additional option, the protrusions 56c may be located on a recessed lingual wall section of the archwire slot, such as the recessed lingual wall sections 46, 46a described above.

The low profile orthodontic appliances according to the invention, including the appliances described in detail above, maybe made of any material that is suitable for use in the oral cavity and has sufficient strength to resist the stresses normally encountered during the course of orthodontic treatment. Examples of such materials include metallic materials such as alloys of stainless steel and titanium. Ceramic materials may also be employed, such as translucent polycrystalline alumina. A particularly preferred low profile orthodontic appliance is made of stainless steel series no. 17-4PH or 316L using a metal injection molding technique.

The orthodontic appliances that are described above are representative examples of the present invention and a number of other embodiments are also possible. For example, the appliances may be adapted for connection to the lingual side of the tooth instead of the labial tooth side as mentioned above. Furthermore, the appliance may be provided with additional features such as auxiliary slots, hooks, alignment marks and the like. Accordingly, the invention should not be deemed limited to the particular examples that are set out in detail, but instead only by a fair scope of the claims that follow along with their equivalents.

What is claimed is:

1. An orthodontic appliance comprising:
    a base having a first, tooth-facing side and a second side opposite the first side, the base also having a number of cavities extending from the first side in a direction toward the second side, wherein the cavities have a certain overall depth in a buccolabial-lingual direction;
    an archwire support connected to the second side of the base, the support having an occlusal wall section and a gingival wall section; and
    an archwire slot extending between the occlusal wall section and the gingival wall section in a generally mesial-distal direction, the archwire slot having a tooth-facing side, wherein the base has a certain thickness in directions along a buccolabial-lingual reference axis between the first side and the second side, wherein the thickness of the base in at least one region next to the tooth-facing side of the archwire slot is less than the thickness of the base in at least one remaining region of the base, and wherein the overall depth of at least some of the cavities varies in corresponding relationship to the variance or the thickness of the base.

2. An orthodontic appliance according to claim 1 wherein the first side of the base has a concave configuration, and wherein the thickness of the base next to the tooth-facing side of the archwire slot is less in regions adjacent the mesial-distal center of the base than the thickness of the base in remaining regions along the archwire slot.

3. An orthodontic appliance according to claim 1 wherein the appliance is a molar appliance.

4. An orthodontic appliance according to claim 1 wherein at least some of the cavities comprise elongated grooves.

5. An orthodontic appliance according to claim 4 wherein at least some of the grooves communicate with each other.

6. An orthodontic appliance according to claim 4 wherein the grooves are not in communication with each other.

7. An orthodontic appliance according to claim 1 wherein at least some of the cavities comprise a series of recesses.

8. An orthodontic appliance according to claim 7 wherein the recesses do not communicate with each other.

9. An orthodontic appliance according to claim 1 wherein the archwire slot has a longitudinal axis and wherein the overall depth of the cavities varies along the longitudinal axis.

10. An orthodontic appliance according to claim 1 wherein the archwire slot has a longitudinal axis and wherein the thickness of the base varies along the longitudinal axis.

11. An orthodontic appliance according to claim 1 wherein the archwire slot has a longitudinal axis and wherein the thickness of the base varies along an axis that is transverse to the longitudinal axis.

12. An orthodontic appliance according to claim 1 wherein the archwire slot has a buccolabial side that is open.

13. An orthodontic appliance according to claim 1 wherein the archwire slot has a buccolabial side that is closed.

14. An orthodontic appliance according to claim 1 wherein the second side of the base includes at least one protrusion extending outwardly in a direction toward the archwire slot.

15. An orthodontic appliance according to claim 14 wherein the protrusion includes a curved surface that faces the archwire slot.

16. An orthodontic appliance according to claim 14 wherein at least one protrusion is offset in directions along a mesial-distal reference axis from the mesial-distal center of the archwire slot.

17. An orthodontic appliance comprising:
    a base having a tooth-facing surface, the base also having a number of cavities with a certain overall depth in a buccolabial-lingual direction;
    an archwire support connected to the base, the support having an occlusal wall section and a gingival wall section; and
    an archwire slot extending between the occlusal wall section and the gingival wall section in a generally mesial-distal direction, the archwire slot having a tooth-facing side, wherein the base has a certain thickness in directions along a buccolabial-lingual reference axis, wherein the axis, wherein the thickness varies in regions next to the tooth-facing side of the archwire slot, and wherein the overall depth of at least some of the cavities varies in corresponding relationship to the variance of the thickness of the base.

18. An orthodontic appliance according to claim 17 wherein the archwire slot has a longitudinal axis and wherein the thickness of the base varies along the longitudinal axis.

19. An orthodontic appliance according to claim 17 wherein the archwire slot has a longitudinal axis and wherein the thickness of the base varies along an axis that is transverse to the longitudinal axis.

20. An orthodontic appliance according to claim 17 wherein the appliance comprises a metal injection molded material.

21. An orthodontic appliance according to claim 17 wherein at least some of the cavities comprise elongated grooves.

22. An orthodontic appliance according to claim 21 wherein at least some of the grooves communicate with each other.

23. An orthodontic appliance according to claim 21 wherein the grooves are not in communication with each other.

24. An orthodontic appliance according to claim 17 wherein at least some of the cavities comprise a series of recesses.

25. An orthodontic appliance according to claim 24 wherein the recesses do not communicate with each other.

26. An orthodontic appliance according to claim 17 wherein the archwire slot has a longitudinal axis and wherein the overall depth of the cavities varies along the longitudinal axis.

27. An orthodontic appliance according to claim 17 wherein the appliance comprises an injection-molded metallic alloy.

28. An orthodontic appliance according to claim 17 wherein the archwire slot has a buccolabial side that is open.

29. An orthodontic appliance according to claim 17 wherein the archwire slot has a buccolabial side that is closed.

30. An orthodontic appliance according to claim 17 wherein the occlusal wall section and the gingival wall section are flat and lie in parallel planes.

31. An orthodontic appliance according to claim 17 wherein the archwire support comprises one or more tiewings.

32. An orthodontic appliance according to claim 17 wherein the archwire support comprises a tube having a passageway presenting the archwire slot.

33. An orthodontic appliance according to claim 17 wherein the tooth-facing surface has a concave configuration.

34. An orthodontic appliance according to claim 17 wherein the base has a side opposite the tooth-facing surface with at least one protrusion extending outwardly in a direction toward the archwire slot.

35. An orthodontic appliance according to claim 34 wherein at least one protrusion includes a curved surface that faces the archwire slot.

36. An orthodontic appliance according to claim 34 wherein at least one protrusion comprises a platform of uniform thickness.

37. An orthodontic appliance according to claim 34 wherein at least one protrusion comprises a ramp of varying thickness.

38. An orthodontic appliance according to claim 34 wherein at least one protrusion comprises a post.

39. An orthodontic appliance according to claim 34 wherein at least one protrusion is offset in direction along a mesial-distal reference axis from the mesial-distal center of the archwire slot.

40. An orthodontic appliance comprising:
a base having a first, tooth-facing side and a second side opposite the first side, the base also having a number of cavities extending from the first side in a direction toward the second side, wherein the cavities have a certain overall depth in a buccolabial-lingual direction;
an archwire support connected to the second side of the base; and
an archwire slot extending across the appliance in a generally mesial-distal direction, wherein the archwire slot has a side next to the tooth that extends along a path located at least partially between the first side and the second side of the base, and wherein at least some of the cavities located in regions lingually of the archwire slot have an overall depth that is less than the overall depth of the cavities located in regions offset from the archwire slot.

41. An orthodontic appliance according to claim 40 wherein the archwire slot has a longitudinal axis and wherein the thickness of the base varies along the longitudinal axis.

42. An orthodontic appliance according to claim 40 wherein the archwire slot has a longitudinal axis and wherein the thickness of the base varies along an axis that is transverse to the longitudinal axis.

43. An orthodontic appliance according to claim 40 wherein the appliance comprises a metal injection molded material.

44. An orthodontic appliance according to claim 40 wherein the archwire slot has a buccolabial side that is open.

45. An orthodontic appliance according to claim 40 wherein the archwire slot has a buccolabial side that is closed.

46. An orthodontic appliance according to claim 40 wherein the base has a side opposite the tooth-facing surface with at least one protrusion extending outwardly in a direction toward the archwire slot.

47. An orthodontic appliance comprising:
a base having a tooth-facing surface;
an archwire support connected to the base for receiving an archwire; and
an archwire slot extending across the archwire support in a generally mesial-distal direction, wherein the base has a plurality of cavities having a certain overall depth in directions along a buccolabial-lingual reference axis, and wherein the overall depth of some of the cavities located in regions lingually of the archwire slot is less than the overall depth of at least some of the remaining cavities located in regions lingually of the archwire slot.

48. An orthodontic appliance according to claim 47 wherein the base has a certain thickness in directions along a buccolabial reference axis, and wherein the overall depth of the cavities varies in corresponding relationship to the variance of the thickness of the base.

49. An orthodontic appliance according to claim 47 wherein at least some of the cavities comprise elongated grooves.

50. An orthodontic appliance according to claim 47 wherein at least some of the grooves communicate with each other.

51. An orthodontic appliance according to claim 47 wherein the grooves are not in communication with each other.

52. An orthodontic appliance according to claim 47 wherein at least some of the cavities comprise an array of spaced apart recesses.

53. An orthodontic appliance according to claim 47 wherein the overall depth of the cavities is the least in regions located lingually of the mesial-distal center of the archwire slot.

54. An orthodontic appliance according to claim 47 wherein the overall depth of the cavities is the least in regions that are located lingually adjacent at least one end of the archwire slot.

55. An orthodontic appliance according to claim 47 wherein the base includes at least one protrusion extending in a direction toward the archwire slot.

56. An orthodontic appliance comprising:

a base having a first, tooth-facing side and a second side opposite the first side;

at least two tiewings directly connected to the base, each of the tiewings having an overall, generally "L"-shaped configuration; and an archwire slot extending across the appliance and between at least two of the tiewings in a generally mesial-distal direction, wherein the archwire slot has a tooth-facing side defined by the second aide of the base and is not spaced in a buccolabial direction from the second side of the base.

57. An orthodontic appliance according to claim 56 wherein the tiewings are integral with the base.

58. An orthodontic appliance according to claim 56 wherein the archwire slot has a side next to he tooth that extends along a path located at least partially between the first side and the second side.

59. An orthodontic appliance according to claim 58 wherein the tiewings are made integral with the base.

60. An orthodontic appliance according to claim 56 wherein the base includes a number of cavities extending from the first side in a direction toward the second side.

61. An orthodontic appliance according to claim 60 wherein the cavities have a certain overall depth in a buccolabial-lingual direction, and wherein at least some of the cavities are located in regions lingually of the archwire slot have an overall depth that is less than the overall depth of cavities located in regions offset from the archwire slot.

62. An orthodontic appliance according to claim 56 wherein the base includes at least one protrusion that extends from the second side toward the archwire slot.

* * * * *

UNITED STATES PATENT AND TRADEMARK OFFICE
CERTIFICATE OF CORRECTION

PATENT NO.   : 6,910,884 B2
DATED        : June 28, 2005
INVENTOR(S)  : Kelly, John S.

It is certified that error appears in the above-identified patent and that said Letters Patent is hereby corrected as shown below:

Column 6,
Line 66, delete "It" and insert -- it --, therefor.

Column 10,
Line 6, delete "or" and insert -- of --, therefor.

Column 13,
Line 24, delete "aide" and insert -- side --, therefor.

Column 14,
Line 6, delete "he" and insert -- the --, therefor.
Line 10, after "are" delete "made".

Signed and Sealed this

Thirtieth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,910,884 B2
DATED : June 28, 2005
INVENTOR(S) : Kelly, John S.

It is certified that error appears in the above-identified patent and that said Letters Patent is hereby corrected as shown below:

Column 10,
Line 65, delete "axis, wherein the" before "thickness".

Signed and Sealed this

Fourth Day of October , 2005

JON W. DUDAS
*Director of the United States Patent and Trademark Office*